United States Patent [19]

Motoyama et al.

[11] Patent Number: 4,820,442
[45] Date of Patent: Apr. 11, 1989

[54] PRESERVATIVE COMPOSITION

[75] Inventors: Shimesu Motoyama; Shigeru Ohno; Seiichi Umeda, all of Tokyo, Japan

[73] Assignee: Freund Industrial Co., Ltd., Tokyo, Japan

[21] Appl. No.: 945,364

[22] Filed: Dec. 22, 1986

[30] Foreign Application Priority Data

Dec. 26, 1985 [JP] Japan .................................. 60-292199
Mar. 19, 1986 [JP] Japan .................................. 61-59367
May 7, 1986 [JP] Japan .................................. 61-103153

[51] Int. Cl.$^4$ .............................................. C09K 15/18
[52] U.S. Cl. .......................... 252/188.28; 252/400.53; 252/401; 423/219; 426/541; 426/544
[58] Field of Search ...................... 252/188.28, 400.53, 252/401, 400.1; 423/219

[56] References Cited

U.S. PATENT DOCUMENTS 4,127,503 11/1978 Yoshikawa et al. ............ 252/188.28
4,230,595 10/1980 Yamaji et al. .................. 252/188.28
4,766,229 8/1988 Kobayashi et al. ......... 252/188.28 X

FOREIGN PATENT DOCUMENTS 54-438 1/1979 Japan .
54-11089 1/1979 Japan .
55-2273 1/1980 Japan .
55-109444 8/1980 Japan .
56-148271 11/1981 Japan .

OTHER PUBLICATIONS

Chem. Ab., 98(26):216394 (1983), B. A. Bolto et al., in *Desalination*, 42(3), p. 273, 1982.

*Primary Examiner*—John F. Terapane
*Assistant Examiner*—Virginia B. Caress
*Attorney, Agent, or Firm*—Kane, Dalsimer, Sullivan, Kurucz, Levy, Eisele and Richard

[57] ABSTRACT

Disclosed is a preservative composition for foodstuffs and the like, which is comprised of (i) a metal powder or a granulated product thereof, (ii) an oxidation accelerator for the metal, (iii) polyallylamine, and (iv) an optional ethanol vapor-generating member. The polyallylamine is preferably deodorized by loading a solution of polyallylamine or a salt thereof on a carrier, and heating and drying the polyallylamine-loaded carrier.

7 Claims, No Drawings

PRESERVATIVE COMPOSITION

BACKGROUND OF THE INVENTION (1) Field of the Invention

The present invention relates to a novel preservative composition for protecting foodstuffs, agricultural products, marine products, livestock products, furs, natural fibers, paper products, and processed products thereof from the adverse effects of microorganisms and insects and the undesirable influences thereon occurring in the presence of oxygen.

(2) Description of the Related Art

As the agent to be used for protecting foodstuffs and the like from the adverse effects of microorganisms or insects by direct incorporation or impregnation, a variety of so-called mildewproofing agents, mothproofing agents and antiseptic agents are known. All of these agents, however, are chemical substances which are more or less toxic, and when introduced into human bodies orally or by inhalation, have undesirable effects on the health.

An oxygen-scavenging composition comprising a metal powder or granule such as iron powder and an alkali metal halide or alkaline earth metal halide (for example, sodium chloride) as an oxidation accelerator has been used as a preservative agent for foodstuffs and the like. More specifically, this oxygen-scavenging composition is packaged in a gas-permeable vessel, and the packaged composition and a foodstuff, an agricultural product, a fur, a natural fiber, a paper product or a processed product are sealed in a gas-barrier vessel, and in this manner, the above-mentioned oxygen-scavenging composition is widely and practically used as a preservative agent for protecting the product from damage by microorganisms such as mildew, insects such as weevils, and oxygen. When, however, the oxygen-scavenging composition is used for a product for which softness is required, such as bread, a Japanese steamed cake or fur, hardening occurs and the taste or texture is degraded. Moreover, in the case of seaweeds such as *Undaria pinnatifida*, browning is caused and the commercial value is lost. Furthermore, the metal surface reacts with water to form a metal oxide and generate hydrogen, and if iron is used as the metal, iron reacts with oxygen or moisture in air to form an oxide and cause rusting, and therefore, red rust spots appear and there is a risk that a fine rust will leak into the vessel.

A preservative composition comprising an ethanol vapor-generating member was proposed (see Japanese Pat. No. 1,046,326) and has been practically used. However, this preservative composition has a problem such that in the case of a foodstuff having a very high water activity, a large amount of the ethanol vapor-generating member must be used.

Utilization of an oxygen-scavenging agent and an ethanol vapor-generating member in combination was tried, but this could not be put into practical application because ethanol vapor introduced in the deoxidizing reaction system (in the deoxidizing agent) was oxidized to form acetaldehyde and this acetaldehyde had an inherent unpleasant smell and was toxic [Text III-20 of 1983 Institute of Support and Development of Technical Research, Tochigi Prefectural Food Industry Advisory Committee (October 1984)].

SUMMARY OF THE INVENTION

It is a primary object of the present invention to provide a preservative composition for foodstuffs, and the like, which is safe and clean and in which the foregoing defects of the conventional preservative compositions are obviated.

In accordance with one fundamental aspect of the present invention, there is provided an oxygen-scavenging composition comprising a metal powder or a granulation product thereof, an oxidation accelerator for the metal, and polyallylamine.

In accordance with another aspect of the present invention, there is provided an oxygen-scavenging composition comprising a metal powder or a granulation product thereof, an oxidation accelerator for the metal, an ethanol vapor-generating member, and polyallylamine.

DESCRIPTION OF THE PREFERRED EMBODIMENTS

The respective components constituting the deoxidizing composition of the present invention will now be described in detail.

[Metal Powder or Granulation Product Thereof and Oxidation Promotor]

A mixture of a metal powder and an oxidation accelerator for the metal powder is used as the oxygen-scavenging agent. As the metal powder, there can be used powders of metals of the groups II through VI and VIII of the fourth period of the Periodic Table. But, in view of the speed of reaction with oxygen and each of control of the reaction speed by adjusting the amount of the oxidation promotor, and from the economical viewpoint, the use of iron powder is most preferred.

As the oxidation accelerator to be used in combination with the metal powder, a metal hydroxide or salt is effectively used. An alkali metal or alkaline earth metal halide is most preferred because it is very easily available.

The presence of water is an important factor for the reaction of the metal powder with oxygen in the atmosphere, in addition to the presence of the oxidation accelerator, and the reaction does not occur in the anhydrous state. If, however, moisture is present in the atmosphere when the oxygen-scavenging agent is used, the reaction is sufficiently advanced, and therefore, water need not be particularly added to the oxygen-scavenging agent. When, however, the present invention is applied to a product which is free of water and is readily deteriorated in air by oxidation, such as an oil or fat, or when it is necessary to promptly remove oxygen, water is incorporated into the oxygen-scavenging agent or water is incorporated into the ethanol vapor-generating member or polyallylamine to be used in combination with the oxygen-scavenging agent. Alternatively, a method may be adopted in which water is adsorbed by paper, cotton, cloth or foam, or a carrier such as silica, alumina, active carbon, diatomaceous earth, bentonite, clay, talc or zeolite, and the water-absorbed member is added to the oxygen-scavenging agent.

[Polyallylamine]

The molecular weight of the polyallylamine used in the present invention is not particularly critical, but preferably a polyallylamine having a molecular weight of at least 2,000 is used.

The mechanism of the reaction of the polyallylamine with the iron powder has not been completely elucidated, but in view of the fact that the formation of reddish-brown rust is controlled and the generation of hydrogen is remarkably reduced, it is considered that the formation of iron oxide is probably controlled by the polyallylamine. Furthermore, the polyallylamine is advantageous in that this action has no influence on the oxygen-removing capacity of the oxygen-scavenging composition. Moreover, where an alcohol is present in the system, the alcohol is prevented from becoming a source of another unpleasant smell by the presence of the polyallylamine. It is presumed that this effect is due to the oxidation of the alcohol to an aldehyde by oxygen in the presence of the oxide of the metal powder is controlled by the presence of the polyallylamine, or the polyallylamine reacts with the formed aldehyde to convert it to a substance having no smell. By dint of this characteristic of the polyallylamine, when the oxygen-scavenging composition is used for the preservative of a foodstuff, even if the foodstuff contains an alcohol or even if an alcohol is used in combination for the preservation, an unpleasant smell is not generated. This is another advantage attained by the present invention.

The polyallylamine may be directly added or a method may be adopted in which the polyallylamine is formed into a solution, the solution is adsorbed by a carrier such as a porous adsorbent and the polyallylamine is added in the adsorbed state. Preferably an anion exchange resin formed by crosslinking the polyallylamine is used.

Most preferably, a product having no smell, which is obtained by making a polyallylamine solution adsorbed in a porous adsorbent and heating and drying the adsorbent to remove an unpolymerized monomer or volatile oligomer, is used. The unpolymerized monomer or volatile oligomer has a strong, unpleasant smell, and the presence of this monomer or oligomer should be particularly avoided when the oxygen-scavenging composition is used for the preservation of a foodstuff or the like.

During our research into the development of a method for deodorizing polyallylamine or its salt, we found that if a solution of polyallylamine or its salt is adsorbed and supported in a porous adsorbent and the adsorbent is then dried, the smell can be easily and completely removed. This deodorization method will now be described.

Available industrial products of polyallylamine or a salt thereof inherently have a strong, unpleasant smell. It is considered that this unpleasant smell is probably due to an unpolymerized monomer or volatile oligomer present in a minute amount in the polyallylamine or the salt thereof. However, it is very difficult to remove the monomer or oligomer to an extent such that the smell is not substantially noticed according to the conventional technique, because the desired polymer is chemically very similar to the monomer or oligomer to be removed.

According to this deodorization method, a solution of polyallylamine or a salt thereof such as a hydrochloride, sulfate or nitrate, is supported in a carrier. Any solvent inert to the polyallylamine or a salt thereof, such as water and lower alcohols, can be used as the solvent for the formation of the solution; water being especially preferred. The amount of the solvent used is not particularly critical. As the carrier, there can be used silica, alumina, active carbon, zeolite, diatomaceous earth, pulp powder, paper, and fabric. Either a powdery carrier or a granular carrier can be used. In order to load the polyallylamine or a salt thereof on the above-mentioned carrier, it is sufficient if a solution of the polyallylamine or its salt is incorporated in and mixed with the carrier. Furthermore, a method may be adopted in which the carrier is charged in a fluidized bed apparatus and a solution of the polyallylamine or a salt thereof is sprayed on the carrier being fluidized.

The polyallylamine-located carrier is then heated and dried. This drying is accomplished by known methods such as stationary drying, stirring drying, atmospheric pressure drying, vacuum drying, and fluidized bed drying. The allowable highest drying temperature varies according to the drying method. In each method, however, the drying must be carried out in air, the temperature must be lower than 150° C., and in the case of vacuum drying, the temperature must be lower than 180° C. If the temperature is higher than this critical level, the intended polyallylamine or salt thereof is deteriorated by oxidation, decomposition or condensation during the operation. Preferably, the drying is carried out at a temperature of 60° to 130° C.

The polyallylamine or a salt thereof may be used when adsorbed and supported in the thus-dried carrier. If it is necessary to use the polyallylamine or a salt thereof in the pure form, the polyallylamine or a salt thereof must be extracted from the carrier with water or a solvent such as a lower aliphatic alcohol, and if desired, the extract concentrated and dried.

[Ethanol Vapor-Generating Member]

Any of paper, cotton, fabric or foam impregnated with ethanol, a powder or granule of silica, alumina, active carbon, diatomaceous earth, bentonite, clay, talc, zeolite, α-starch, dextrin or powder cellulose having ethanol absorbed or adsorbed therein, an microencapsulation product of ethanol (Japanese Unexamined Patent Publication No. 60-99337), and a compound capable of forming and releasing ethanol by chemical reaction with water in air or water evaporated from a foodstuff or the like, such as a compound having an ethoxyl group connected to a metal atom such as silicon, titanium or tin (Japanese Examined Patent Publication No. 61-47806), can be optionally used as the ethanol-generating member in the present invention.

The powder or granule having ethanol adsorbed or absorbed therein or the microencapsulation product of ethanol by using such powder or granule is suitable for industrial mass-production and has a large capacity of adsorbing or absorbing ethanol per unit weight of the powder or granule. Namely, even if 2 to 2.5 cc of ethanol is adsorbed per gram of the powder or granule, the ethanol-adsorbed powder or granule remains dry and free-flowing and is easily adapted to a high speed automatic packaging operation.

Preferably ethanol having a concentration of at least 60% by weight is used.

The ethanol vapor-generating member, the oxygen-scavenging agent and the polyallylamine may be packed and sealed independently or in combination (any two components of the above three components may be combined or all of the three components may be combined) in a gas-permeable vessel such as a paper bag or a bag made of paper laminated with polyethylene or the like, and this air-permeable vessel sealed together with a foodstuff or the like into a preserving vessel or a bag for foodstuff or the like.

When the oxygen-scavenging agent is packed in a vessel for foodstuff or the like, especially in a bag, hydrogen is generated and the bag in which the oxygen-scavenging agent is sealed becomes swollen, and moreover, the bag in which the foodstuff or the like is sealed is similarly swollen by hydrogen leaking from the bag of the oxygen-scavenging agent. If however, the polyallylamine is incorporated in the oxygen-scavenging agent, the formation of hydrogen is prevented and the aldehyde formed by contact between ethanol vapor and the metal powder is immediately fixed by the polyallylamine. Accordingly, preferably the polyallylamine is incorporated at least in the oxygen-scavenging agent.

The amounts of the respective components in the reservative composition of the present invention are preferably such that the amounts of (i) the metal powder or the granulated product thereof, (ii) an oxidation accelerator for the metal and (iii) polyallylamine are 60 to 80% by weight, 1 to 40% by weight and 0.1 to 10% by weight, respectively, based on the sum of the components (i), (ii) and (iii).

Where the preservative composition of the present invention further comprises (iv) the ethanol vapor-generating member, it is preferable that the amounts of (i) the metal powder or the granulated product thereof, (ii) an oxidation accelerator for the metal, (iii) polyallylamine and (iv) the ethanol vapor-generating member are 1 to 80% by weight, 0.5 to 20% by weight, 0.1 to 10% by weight and 2 to 70% by weight as the amount of ethanol contained in the component (iv), respectively, based on the sum of the components (i) through (iv).

Where the ethanol vapor-generating member, the oxygen-scavenging agent, and the polyallylamine are together sealed in a gas-permeable bag and used as a food preservative agent, if the amount of ethanol or the amount of ethanol formed by the chemical reaction is smaller than 2% by weight (all of "%" given hereinafter are by weight) based on the food preservative composition, the effect of controlling the activity of a microorganism or insect, or the effect of retaining a desired softness in a fur, bread or the like, is reduced, although the above-mentioned critical amount varies to some extent according to the amount of the preservative agent used.

If the amount of the metal powder is smaller than 1% based on the sum of all the components of the preservation composition, the oxygen-scavenging effect is too low and the activity of a microorganism or insect is not sufficiently controlled. If the amount of the oxidation accelerator is smaller than 1% based on the metal powder, the oxidation-accelerating effect is too low for practical purposes. Even if the polyallylamine is incorporated in a minute amount, the polyallylamine exerts the intended effect, and it is sufficient if the polyallylamine is used in an amount of at least 0.5% based on the metal powder.

The preservative composition of the present invention is effective as a preservative agent for foodstuffs shown in the examples, other foodstuffs, agricultural products, marine products, livestock products, furs, leathers, wool, natural fibers, and processed products thereof.

The present invention will now be described in detail with reference to the following examples that by no means limit the scope of the invention.

In the example, the state of the formation of red rust was evaluated according to the following 3-stage rating method:
(−): no red rust
(+): some red rust
(++): extreme red rust The smell (organoleptic test) was evaluated according to the following 4-stage rating method:
(−): no smell
(±): slight smell
(+): some smell
(++): strong smell The preparation of an odorless polyallylamine or salt-supporting carrier will first be described with reference to the following referential examples.

REFERENTIAL EXAMPLE 1

In 500 ml of water was dissolved 100 g of polyallylamine hydrochloride (PAA-HCl-10S supplied by Nitto Boseki Co.), 436 g of a 10% aqueous solution of caustic soda was added to the solution, and the mixture was stirred for about 10 minutes to form an aqueous solution of free polyallylamine. This aqueous solution had an extreme amine-like unpleasant smell.

The aqueous solution was gradually poured into 1,000 g of powdery silica (Adsolider 101 supplied by Freund Industrial Co., Ltd.) and the mixture was gently stirred to adsorb and support the polyallylamine on the silica and obtain a powdery composition. This composition also had an unpleasant smell similar to that of the aqueous solution of the polyallylamine.

The composition was charged in a stainless steel vat and spread therein, and the composition was dried for 5 hours in an air drier maintained at 105° C. to obtain 1,052 g of a silica powder loaded with the polyallylamine. The powder had no smell at all.

REFERENTIAL EXAMPLE 2

To 1.0 part by weight of an aqueous solution of polyallylamine hydrochloride (PAA-HCl-10L supplied by Nitto Boseki Co., concentration=50%) was added 2.2 parts by weight of a 10% aqueous solution of NaOH, and the mixture was stirred to form an aqueous solution of free polyallylamine. This aqueous solution had a very unpleasant smell. This aqueous solution was homogeneously mixed with 5.0 parts by weight of powder silica (Adsolider 101 supplied by Freund Industrial Co., Ltd.) with stirring and the mixture was air-dried at 105° C. for 5 hours to obtain a composition loaded with the free polyallylamine. This composition also had a similar unpleasant smell.

The composition was dried in the same manner as described in Referential Example 1 to obtain a polyallylamine-loaded silica powder.

Polyallylamine-loaded powders were prepared in the same manner as described above except that powdery active carbon (supplied by Takeda Chem. Ind. Ltd.) or powdery zeolite (supplied by Mizushima Kagaku) was used instead of the powdery silica.

Each of the dried carriers was smellless.

REFERENTIAL EXAMPLE 3

To 100 g of an aqueous solution of polyallylamine hydrochloride (PAA-HCl-10L supplied by Nitto Boseki, concentration=40%) was added 175 g of a 10% aqueous solution of caustic soda with stirring, and the mixture was stirred for 10 minutes to form an aqueous solution of free polyallylamine. The aqueous solution had a very unpleasant smell.

The aqueous solution was poured into 500 g of alumina for chromatography and the mixture was stirred to adsorb and support the polyallylamine on the alumina. The obtained polyallylamine-loaded composition had a similar unpleasant smell.

The composition was charged in a "FLOW COATER" (trade name; fluidized bed coating apparatus Model MINI supplied by Freund Industrial Co., Ltd.) and the composition was dried for 2 hours under circulation of hot air maintained at 120° C. to obtain 506 g of an alumina powder loaded with the polyallylamine. The powder was odorless but a substance having the above-mentioned unpleasant smell was expelled from an exhaust opening of the FLOW COATER.

REFERENTIAL EXAMPLE 4

In the same manner as described in Referential Example 1, 1036 g of an aqueous solution of polyallylamine was prepared. This aqueous solution had a very unpleasant smell. Then, the aqueous solution was mixed with 1 kg of a pulp powder (KC-Floc supplied by Sanyo Kokusaku Pulp Co.) to adsorb the polyallylamine on the pulp powder. The resultant composition also had a very unpleasant smell.

The composition was spread in a stainless steel vat and dried at 80° C. overnight in a vacuum drier to obtain 1,015 g of a powder loaded with the polyallylamine. The obtained powder had no smell.

To 100 g of the thus-obtained dry powder, 500 ml of ethanol was added, and the mixture was stirred for 1 hour and subjected to suction filtration using a Buchner funnel. The filtrate was concentrated and dried by a rotary evaporator to obtain 5.1 g of polyallylamine. The obtained polyallylamine had no smell at all.

REFERENTIAL EXAMPLE 5

To 100 g of an aqueous solution of polyallylamine hydrochloride (concentration=50%) was added 150 g of water, the solution diluted to a concentration of 20% was gradually poured into 150 g of powdery silica (Adsolider 101; supplied by Freund Industrial Co., Ltd.), and the mixture was gradually stirred to load the polyallylamine hydrochloride on the silica. The resultant composition was spread in a stainless steel vat and dried for 4 hours in a tray drier maintained at 100° C. while the composition was occasionally stirred, whereby 205 g of silica loaded with the polyallylamine hydrochloride was obtained. The dry product was neutralized with 220 ml of a 10% aqueous solution of caustic soda. The neutralization product had no smell at all.

EXAMPLES 1 THROUGH 6 AND COMPARATIVE EXAMPLES 1 THROUGH 3

Iron powder, a metal chloride as the oxidation accelerator, and the polyallylamine-loaded silica powder obtained in Referential Example 1 were mixed according to a recipe shown in Table 1 to obtain an oxygen-scavenging composition. In order to use the oxygen-scavenging composition as a preservative agent, the oxygen-scavenging composition was packed in a pouch of a laminate of rayon paper and a porous polyethylene film and the pouch was heat-sealed. This sealed pouch and six commercially available rice cake slices (270 g) were then charged and sealed in a bag having a capacity of 1.2 l, which was composed of a nylon/polyethylene laminate film coated with polyvinylidene chloride. The sealed bag was stored at room temperature, and the preservative effect, oxygen-removing capacity, formation of red rust, and hydrogen concentration were determined.

For comparison, the experiment was similarly carried out by using iron powder and the oxidation accelerator alone.

The obtained results are shown in Table 1.

TABLE 1

| | Amount of iron Powder (g) | Kind and amount of oxidation accelerator (g) | | Amount of polyallylamine *(mg) | Formation of red rust (after 10 days) | $O_2$ concentration (after 2 days) | $H_2$ concentration | | Preservation effect |
|---|---|---|---|---|---|---|---|---|---|
| | | | | | | | After 2 days (%) | After 10 days (%) | |
| Example 1 | 20 | NaCl | 1.0 | 30 | — | less than 0.01% | 0.16 | 0.24 | Not mildewed for 1 month |
| Example 2 | 20 | NaCl | 1.0 | 50 | — | less than 0.01% | 0.13 | 0.20 | Not mildewed for 1 month |
| Example 3 | 20 | KCl | 1.0 | 30 | — | less than 0.01% | 0.15 | 0.28 | Not mildewed for 1 month |
| Example 4 | 20 | KCl | 1.0 | 50 | — | less than 0.01% | 0.11 | 0.26 | Not mildewed for 1 month |
| Example 5 | 20 | $CaCl_2$ | 1.0 | 30 | — | less than 0.01% | 0.10 | 0.18 | Not mildewed for 1 month |
| Example 6 | 20 | $CaCl_2$ | 1.0 | 50 | — | less than 0.01% | 0.08 | 0.15 | Not mildewed for 1 month |
| Comparative Example 1 | 20 | NaCl | 1.0 | 0 | ++ | less than 0.01% | 2.4 | 3.6 | Not mildewed for 1 month |
| Comparative Example 2 | 20 | KCl | 1.0 | 0 | ++ | less than 0.01% | 2.8 | 4.2 | Not mildewed for 1 month |
| Comparative Example 3 | 20 | $CaCl_2$ | 1.0 | 0 | ++ | less than 0.01% | 2.5 | 4.0 | Not mildewed for 1 month |
| Comparative Example 4 | — | — | | — | — | 23.2% | 0.0 | 0.0 | Mildewed in 5 days |

*Amount (mg) of free polyallylamine-loaded on silica

EXAMPLES 7 AND 8 AND COMPARATIVE EXAMPLES 5 THROUGH 8

The preservative agent formed by using the oxygen-scavenging composition prepared in Example 1 and 200 g of a brandy cake or chocolate cake was charged and sealed in a bag having a capacity of 1.0 l, which was composed of a nylon-polyethylene laminate film coated with polyvinylidene chloride. The bag was stored at room temperature, and the preservative effect, formation of red rust, and generation of hydrogen were checked. Furthermore, the organoleptic test was carried out with respect to the smell.

The experiment was similarly carried out by using the preservative agent of Comparative Example 1 (Comparative Examples 5 and 7), or without using the oxygen-scavenging agent (Comparative Examples 6 and 8).

The obtained results are shown in Tables 2 and 3.

iron powder, and sodium chloride were homogeneously mixed according to a recipe shown in Table 4. The resulting powdery composition was charged into a pouch composed of a laminate of rayon paper and a porous polyethylene film and the pouch was heat-sealed. The sealed pouch and four commercially available rice cake slices (180 g) were then charged and

TABLE 2

|   | Amount of iron powder (g) | Amount of sodium chloride (g) | Amount of polyallylamine (mg) | Number of elapsing days | Smell | Red rust | $H_2$ concentration (%) | Preservative effect |
|---|---|---|---|---|---|---|---|---|
| Example 7 | 2.0 | 1.0 | 30 | 2 | — | — | 0.018 | Formation of mildew |
|  |  |  |  | 6 | — | — | 0.026 | and putrefaction were |
|  |  |  |  | 10 | — | — | 0.050 | not observed even |
|  |  |  |  | 180 | — | — | 0.072 | after 6 months |
| Comparative Example 5 | 2.0 | 1.0 | 0 | 2 | ++ | + | 2.6 | Formation of mildew |
|  |  |  |  | 6 | ++ | ++ | 3.4 | and putrefaction were |
|  |  |  |  | 10 | ++ | ++ | 4.4 | not observed even |
|  |  |  |  | 180 | + | ++ | 6.5 | after 6 months |
| Comparative Example 6 | 0 | 0 | 0 |  |  |  |  | Formation of mildew was observed in 20 days |

TABLE 3

|   | Amount of iron powder (g) | Amount of sodium chloride (g) | Amount of polyallylamine (mg) | Number of elapsing days | Smell | Red rust | $H_2$ concentration (%) | Preservative effect |
|---|---|---|---|---|---|---|---|---|
| Example 8 | 2.0 | 1.0 | 30 | 2 | — | — | 0.020 | Formation of mildew |
|  |  |  |  | 6 | — | — | 0.028 | and putrefaction were |
|  |  |  |  | 10 | — | — | 0.046 | not observed even |
|  |  |  |  | 180 | — | — | 0.068 | after 6 months |
| Comparative Example 7 | 2.0 | 1.0 | 0 | 2 | ++ | + | 2.8 | Formation of mildew |
|  |  |  |  | 6 | ++ | ++ | 3.6 | and putrefaction were |
|  |  |  |  | 10 | ++ | ++ | 4.5 | not observed even |
|  |  |  |  | 180 | + | ++ | 6.5 | after 6 months |
| Comparative Example 8 | 0 | 0 | 0 |  |  |  |  | Formation of mildew was observed in 20 days |

EXAMPLES 9 THROUGH 12 AND COMPARATIVE EXAMPLE 9

To 1.0 part by weight of porous powdery silica (Adsolider 101 supplied by Freund Industrial Co., Ltd.) was gradually added 1.8 parts by weight of ethanol and the mixture was stirred to uniformly support ethanol on the powdery silica and obtain a powdery ethanol-loaded composition. This ethanol-loaded composition as the ethanol vapor-generating member, the polyallylamine-loaded powdery composition, powdery active carbon or powdery zeolite, prepared in Referential Example 2, sealed in a bag having a capacity of 1.2 l, which was composed of a nylon/polyethylene laminate film coated with polyvinylidene chloride. The bag was stored at 25° C., the aldehyde concentration in the bag was measured with the lapse of time, and the organoleptic test of the smell was carried out. The obtained results are shown in Table 4.

For comparison, the experiment was carried out in the same manner as described above except that the polyallylamine-loaded composition was removed from the above-mentioned powdery composition. The obtained results are shown in Table 4.

TABLE 4

|  | Composition | | | | | Acetaldehyde concentration (ppm) and smell | | | | |
|---|---|---|---|---|---|---|---|---|---|---|
|  | Amount of ethanol vapor-generating member (g)** | Amount of iron powder (g) | Amount of sodium chloride (g) | Kind of carrier | Amount of polyallyl-amine (mg)* | 2.5 hours | 5.0 hours | 1 day | 3 days | 10 days |
| Example 9 | 1.0 | 1.0 | 0.2 | Silica | 10 | 20 (+) | 16 (+) | 10 (−) | 10 (−) | 6 (−) |
| Example 10 | 1.0 | 1.0 | 0.2 | Silica | 30 | 8 (−) | 10 (−) | 10 (−) | 8 (−) | 4 (−) |
| Example 11 | 1.0 | 1.0 | 0.2 | Active carbon | 30 | 8 (−) | 9 (−) | 8 (−) | 5 (−) | 5 (−) |
| Example 12 | 1.0 | 1.0 | 0.2 | Zeolite | 30 | 9 (−) | 10 (−) | 8 (−) | 4 (−) | 4 (−) |
| Example 13 | 1.0 | 1.0 | 0.2 | Silica | 50 | 0 (−) | 6 (−) | 6 (−) | 0 (−) | 0 (−) |
| Comparative | 1.0 | 1.0 | 0.2 | — | 0 | 300 | 350 | 380 | 200 | 120 |

TABLE 4-continued

| | Composition | | | | Acetaldehyde concentration (ppm) and smell | | | | |
|---|---|---|---|---|---|---|---|---|---|
| | Amount of ethanol vapor-generating member (g)** | Amount of iron powder (g) | Amount of sodium chloride (g) | Kind of carrier | Amount of polyallyl-amine (mg)* | 2.5 hours | 5.0 hours | 1 day | 3 days | 10 days |
| Example 9 | | | | | | (++) | (++) | (++) | (++) | (++) |

*amount (mg) of loaded free polyallylamine
**amount (g) calculated as ethanol

EXAMPLE 14 AND COMPARATIVE EXAMPLES 10 THROUGH 14

The same ethanol vapor-generating member as used in Examples 9 through 13, the polyallylamine-loaded powdery composition obtained in Referential Example 2, iron powder, and sodium chloride were homogeneously mixed according to a recipe shown in Table 5, and the resulting powdery composition was charged in a pouch composed of a laminate of rayon paper and a porous polyethylene film and the pouch was heat-sealed. The sealed pouch and 60 g of boiled fish paste, i.e., a food product having a high water activity (water activity value=0.92) were charged and sealed in a bag having a capacity of 0.8 l, which was composed of a nylon/polyethylene laminate film coated with polyvinylidene chloride. The bag was stored at 25° C., and the formation of mildew was checked, and the organoleptic test of the smell was carried out.

For comparison, the experiment was carried out in the same manner as described above except that the preservative agent was not used (Comparative Example 10), the ethanol vapor-generating member alone was used as the preservative agent (Comparative Examples 11 and 13), a mixture of the ethanol vapor-generating member with iron powder and sodium chloride was used as the preservative agent (Comparative Example 14), or a mixture of iron powder and sodium chloride was used as the preservative agent (Comparative Example 12).

The obtained results are shown in Table 5.

EXAMPLES 15 AND 16 AND COMPARATIVE EXAMPLES 15 THROUGH 20

A powder of a homogeneous mixture comprising absorbent cotton impregnated with ethanol as the ethanol vapor-generating member, iron powder and a metal chloride, and the polyallylamine-loaded powdery silica or polyallylamine-loaded powdery active carbon obtained in Referential Example 2 were independently packed in pouches composed of a laminate of rayon paper and a porous polyethylene film, and the pouches were heat-sealed. These pouches and 600 g of sponge cake, i.e., a food product having a high water activity (water activity value=0.89) were charged and sealed in a bag having a capacity of 1.0 l, which was composed of a nylon/polyethylene laminate film coated with polyvinylidene chloride. The bag was stored at 25° C., and the formation of mildew and putrefaction were checked, and the organoleptic test of the smell was carried out.

For comparison, the experiment was carried out in the same manner as described above except that the preservative agent was not used (Comparative Example 15), the ethanol vapor-generating member alone was used as the preservative agent (Comparative Examples 16 and 19), the ethanol vapor-generating member was used in combination with iron powder and the metal chloride (Comparative Example 20), or a mixture of iron powder and the metal chloride was used (Comparative Examples 17 and 18).

The obtained results are shown in Table 6.

TABLE 5

| | Composition | | | | | |
|---|---|---|---|---|---|---|
| | Amount of ethanol vapor-generating member (g)** | Amount of iron powder (g) | Amount of sodium chloride (g) | Kind of carrier | Amount of polyallylamine (mg)* | Acetaldehyde concentration (ppm) and smell |
| Example 14 | 1.0 | 1.5 | 0.2 | Silica | 30 | Formation of mildew and putrefaction after 10 days (−) |
| Comparative Example 10 | 0 | 0 | 0 | — | 0 | Formation of mildew and putrefaction after 2 days (−) |
| Comparative Example 11 | 1.0 | 0 | 0 | — | 0 | Formation of mildew and putrefaction after 4 days (−) |
| Comparative Example 12 | 0 | 1.5 | 0.2 | — | 0 | Formation of mildew and putrefaction after 2 days (−) |
| Comparative Example 13 | 3.0 | 0 | 0 | — | 0 | Formation of mildew and putrefaction after 8 days (alcoholic smell) (−) |
| Comparative Example 14 | 1.0 | 1.5 | 0.2 | — | 0 | Formation of mildew and putrefaction after 10 days (++) |

*amount (g) calculated as ethanol
**amount (mg) of loaded free polyallylamine

TABLE 6

| | Composition | | | | | |
|---|---|---|---|---|---|---|
| | Amount of ethanol vapor-generating member (g)* | Amount of iron powder (g) | Kind and amount of metal chloride (g) | Kind of carrier | Amount of polyallylamine (mg)** | Formation of mildew and smell |
| Example 15 | 1.0 | 2.0 | KCl 0.2 | Active carbon | 40 | Formation of mildew and putrefaction after 80 days (−) |
| Example 16 | 1.0 | 2.0 | MgCl$_2$ 0.2 | Silica | 40 | Formation of mildew and |

TABLE 6-continued

| | Composition | | | | | |
|---|---|---|---|---|---|---|
| | Amount of ethanol vapor-generating member (g)* | Amount of iron powder (g) | Kind and amount of metal chloride (g) | Kind of carrier | Amount of polyallylamine (mg)** | Formation of mildew and smell |
| Comparative Example 15 | 0 | 0 | 0 | — | 0 | putrefaction after 90 days (−) Formation of mildew and putrefaction after 20 days (−) |
| Comparative Example 16 | 1.0 | 0 | 0 | — | 0 | Formation of mildew and putrefaction after 30 days (−) |
| Comparative Example 17 | 0 | 2.0 | KCl 0.2 | — | 0 | Formation of mildew and putrefaction after 30 days (−) |
| Comparative Example 18 | 0 | 2.0 | $MgCl_2$ 0.2 | — | 0 | Formation of mildew and putrefaction after 30 days (−) |
| Comparative Example 19 | 3.0 | 0 | 0 | — | 0 | Formation of mildew and putrefaction after 80 days (alcoholic smell) |
| Comparative Example 20 | 1.0 | 2.0 | KCl 0.2 | — | 0 | Formation of mildew and putrefaction after 80 days (−) |

*amount (g) calculated as ethanol
**amount (mg) of loaded free polyallylamine

EXAMPLES 17 AND 18 AND COMPARATIVE EXAMPLES 21 THROUGH 26

An ethanol vapor-generating member was formed by gradually adding 1.0 part by weight of ethanol to 2.0 parts by weight of porous aluminum silicate to support ethanol on the aluminum silicate, and this ethanol vapor-generating member and a homogeneous mixture comprising iron powder, a metal chloride and the polyallylamine-loaded zeolite obtained in Referential Example 2 in amounts shown in Table 7 were individually packed in pouches composed of a laminate of rayon paper and a porous polyethylene film and the pouches were heat-sealed. These pouches and rare cheese cake, i.e., a food product having a high water activity (water activity value=0.94) were charged and sealed in a bag having a capacity of 0.9 l, which was composed of a nylon/polyethylene laminate film coated with polyvinylidene chloride. The bag was stored at 25° C., and the formation of mildew and putrefaction were checked, and the organoleptic test of the smell was carried out.

For comparison, the experiment was carried out in the same manner as described above except that the preservative agent was not used (Comparative Example 21), the ethanol vapor-generating member alone was used as the preservative agent (Comparative Examples 22 and 25), the ethanol vapor-generating member was used in combination with a mixture of iron powder and the metal chloride (Comparative Example 26), or a mixture of iron powder and the metal chloride was used (Comparative Examples 23 and 24).

The obtained results are shown in Table 7.

TABLE 7

| | Composition | | | | | |
|---|---|---|---|---|---|---|
| | Amount of ethanol vapor-generating member (g)* | Amount of iron powder (g) | Kind and amount of metal chloride (g) | Kind of carrier | Amount of polyallylamine (mg)** | Formation of mildew and smell |
| Example 17 | 1.5 | 1.0 | $CaCl_2$ 0.2 | Silica | 40 | Formation of mildew and putrefaction after 6 days (−) |
| Example 18 | 1.5 | 1.0 | $FeCl_3$ 0.3 | Silica | 40 | Formation of mildew and putrefaction after 2 days (−) |
| Comparative Example 21 | 0 | 0 | 0 | — | 0 | Formation of mildew and putrefaction after 2 days (−) |
| Comparative Example 22 | 1.5 | 0 | 0 | — | 0 | Formation of mildew and putrefaction after 2 days (−) |
| Comparative Example 23 | 0 | 1.0 | $CaCl_2$ 0.2 | — | 0 | Formation of mildew and putrefaction after 2 days (−) |
| Comparative Example 24 | 0 | 1.0 | $FeCl_3$ 0.3 | — | 0 | Formation of mildew and putrefaction after 2 days (−) |
| Comparative Example 25 | 4.0 | 0 | 0 | — | 0 | Formation of mildew and putrefaction after 2 days (alcoholic smell) |
| Comparative Example 26 | 1.5 | 1.0 | $CaCl_2$ 0.2 | — | 0 | Formation of mildew and putrefaction after 5 days |

TABLE 7-continued

| | Composition | | | | |
|---|---|---|---|---|---|
| Amount of ethanol vapor-generating member (g)* | Amount of iron powder (g) | Kind and amount of metal chloride (g) | Kind of carrier | Amount of polyallylamine (mg)** | Formation of mildew and smell |
| | | | | | (++) |

*amount (g) calculated as ethanol
**amount (mg) of loaded free polyallylamine

EXAMPLES 19 AND 20 AND COMPARATIVE EXAMPLE 27

Absorbent cotton impregnated with ethanol, a powder of a homogeneous mixture of iron powder and a metal chloride, and the polyallylamine-loaded powdery silica or polyallylamine-loaded powdery active carbon obtained in Referential Example 2 were individually packed in pouches composed of a laminate of rayon paper and a porous polyethylene film and the pouches were heat-sealed. These sealed pouches, a leather glove, and a wool necktie were charged and sealed in a bag having a capacity of 1.0 l, which was composed of a nylon/polyethylene laminate film coated with polyvinylidene chloride. The bag was stored at room temperature from April to November, and the formation of mildew was checked.

For comparison, the experiment was carried out in the same manner as described above except that no component was added.

The obtained results are shown in Table 8.

When a mixture of iron powder and the metal chloride alone was used, the gloss of the leather product was lost after about 3 months.

TABLE 8

| | Composition | | | | |
|---|---|---|---|---|---|
| | Amount of ethanol vapor-generating member (g)* | Amount of iron powder (g) | Kind and amount of metal chloride (g) | Kind of carrier | Amount of polyallylamine (mg)** | Formation of mildew and smell |
| Example 19 | 1.0 | 2.0 | NaCl 0.2 | Silica | 40 | Gloss of leather article was not lost and leather article was not mildewed even after 8 months |
| Example 20 | 1.0 | 2.0 | KCl 0.2 | Active carbon | 40 | Gloss of leather article was not lost and leather article was not mildewed even after 8 months |
| Comparative Example 21 | 0 | 0 | 0 | | 0 | Glove was mildewed after 3 months and necktie was mildewed after 4 months |

*amount (g) calculated as ethanol
**amount (mg) of loaded free polyallylamine

We claim:

1. A preservative composition, which comprises;
   (i) 60% to 98% by weight of an iron powder or a granulated product thereof,
   (ii) 1% to 40% by weight of an alkali metal halide or an alkaline earth metal halide, and
   (iii) 0.1% to 10% by weight of polyallylamine, the amounts of the respective components (i), (ii) and (iii) being based on the sum of the three components (i), (ii) and (iii).

2. A preservative composition as set forth in claim 1, which further comprises (iv) an ethanol vapor-generating member, and wherein the amount of the component (i) is 1 to 80% by weight based on the sum of the components (i) through (iv), the amount of the component (ii) is 0.5 to 20% by weight based on the sum of the components (i) through (iv), the amount of the component (iii) is 0.1 to 10% by weight based on the sum of the components (i) through (iv) and the amount of ethanol contained in the component (iv) is 2 to 70% by weight based on the sum of the components (i) through (iv).

3. A preservative composition as set forth in claim 1, wherein the polyallylamine is loaded on a porous carrier.

4. A preservative composition as set forth in claim 3, wherein the carrier contains water.

5. A preservative composition as set forth in claim 1, wherein the polyallylamine is loaded on a porous carrier and is then heated and dried to effect deodorization.

6. A preservative composition as set forth in claim 1, wherein the ethanol vapor-generating member is formed by loading ethanol on a powdery or granular carrier.

7. A preservative composition as set forth in claim 6, wherein the carrier contains water.

* * * * *

UNITED STATES PATENT AND TRADEMARK OFFICE
CERTIFICATE OF CORRECTION

PATENT NO. : 4,820,442

DATED : April 11, 1989

INVENTOR(S) : Shimesu Motoyama, Shigeru Ohno, Seiichi Umeda, Ryuji Ikema, Shinji Inohana and Masako Hoshino It is certified that error appears in the above-identified patent and that said Letters Patent is hereby corrected as shown below: ON TITLE PAGE:

Change the names of the inventors from "Shimesu Motoyama; Shigeru Ohno; Seiichi Umeda" to -- Shimesu Motoyama, Shigeru Ohno, Seiichi Umeda, Ryuji Ikema, Shinji Inohana and Masako Hoshino --.

Signed and Sealed this

Twenty-third Day of June, 1992

*Attest:*

DOUGLAS B. COMER

*Attesting Officer*     *Acting Commissioner of Patents and Trademarks*